(12) United States Patent
Kang et al.

(10) Patent No.: US 11,060,090 B2
(45) Date of Patent: Jul. 13, 2021

(54) METHOD OF RELEASING THE SUPPRESSION OF EGG MATURATION IN ECONOMICALLY-IMPORTANT PRAWN/SHRIMP SPECIES

(71) Applicant: JAPAN INTERNATIONAL RESEARCH CENTER FOR AGRICULTURAL SCIENCES, Tsukuba (JP)

(72) Inventors: Bong Jung Kang, Tsukuba (JP); Marcy Wilder, Tsukuba (JP)

(73) Assignee: Japan International Research Center for Agricultural Sciences, Ibaraki (JP)

(*) Notice: Subject to any disclaimer, the term of this patent is extended or adjusted under 35 U.S.C. 154(b) by 117 days.

(21) Appl. No.: 16/333,544

(22) PCT Filed: Oct. 27, 2017

(86) PCT No.: PCT/JP2017/038853
§ 371 (c)(1),
(2) Date: Mar. 14, 2019

(87) PCT Pub. No.: WO2018/084077
PCT Pub. Date: May 11, 2018

(65) Prior Publication Data
US 2019/0233819 A1 Aug. 1, 2019

(30) Foreign Application Priority Data
Nov. 1, 2016 (JP) .............................. JP2016-214411

(51) Int. Cl.
| | | |
|---|---|---|
| *A61K 48/00* | (2006.01) | |
| *C07H 21/04* | (2006.01) | |
| *C12N 15/113* | (2010.01) | |
| *A61K 31/713* | (2006.01) | |
| *A01K 61/59* | (2017.01) | |
| *A01K 67/033* | (2006.01) | |

(52) U.S. Cl.
CPC ............ *C12N 15/113* (2013.01); *A01K 61/59* (2017.01); *A61K 31/713* (2013.01); *C12N 15/1136* (2013.01); *A01K 67/033* (2013.01); *C12N 2310/14* (2013.01); *C12N 2320/50* (2013.01); *Y02A 40/81* (2018.01)

(58) Field of Classification Search
CPC .......................... C12N 15/113; C12N 2310/14
See application file for complete search history.

(56) References Cited

U.S. PATENT DOCUMENTS

2015/0099702 A1* 4/2015 Chan ..................... A61K 31/713
514/9.7

FOREIGN PATENT DOCUMENTS

| CN | 104212813 A | 12/2014 |
|---|---|---|
| WO | WO-02/083717 A1 | 10/2002 |

OTHER PUBLICATIONS

Feijo et al. (Mar Biotechnol, 2016, 18, 117-123).*
Feijorg et al., "Silencing of Gonad-Inhibiting Hormone Transcrips in Litopenaeus Vannamei Females by use of the RNA Interference Technology," Marine Biotechnology, 2016, vol. 18, pp. 117-123.
International Search Report dated Jan. 29, 2018, in PCT/JP2017/038853.
Tiu et al., "The Use of Recombinant Protein and RNA Interference Approaches to Study the Reproductive Functions of a Gonad-stimulating Hormone from the Ship Metapenaeus ensis," The FEBS Journal, 2007, 274(2007): 4385-4395.
Treerattrakool et al., "Induction of Ovarian Maturation and Spawning in Penaeus monodon Broodstock by Double-Stranded RNA," Marine Biotechnology, 2011, vol. 13, pp. 163-169.
Treerattrakool et al., "Molecular Characterization of Gonad-inhibiting Hormone of Penaeus Monodon and Elucidation of its Inhibitory Role in Vitellogenin Expression by RNA Interference," The FEBS Journal, 2008, vol. 275, pp. 970-980.
Treerattrakool et al., "Silencing of Gonad-inhibiting Hormone Gene Expression in Penaeus monodon by Feeding with GIH dsRNA-enriched Artemia," Elsevier B.V., 2013, 404-405(2013): 116-121.
Tsutsui et al., "Molecular Cloning of a cDNA Encoding Vitellogenesis-Inhibiting Hormone in the Whiteleg Shrip Litopenaeus Vannamei and Preparation of its recombinant Peptide using an *E. coli* Expression System," The Japanese Society of Fisheries Science, 2013, vol. 79, pp. 357-365.
Tsutsui et al., "Purification of Sinus Gland Peptides Having Vitellogenesis-Inhibiting Activity from the Whiteleg Shrimp *Litopenaeus vannamei*," Marine Biotechnology, 2007, vol. 9, pp. 360-369.
Feijó et al., "Silencing of Gonad-Inhibiting Hormone Transcrips in Litopenaeus Vannamei Females by use of the RNA Interference Technology," Marine Biotechnology, 2016, vol. 18, pp. 117-123.
Tiu et al., "The Use of Recombinant Protein and RNA Interference Approaches to Study the Reproductive Functions of a Gonad-stimulating Hormone from the Shrimp *Metapenaeus ensis*," The FEBS Journal, 2007, 274(2007): 4385-4395.

(Continued)

*Primary Examiner* — Amy H Bowman
(74) *Attorney, Agent, or Firm* — Foley & Lardner LLP

(57) ABSTRACT

An object of the present invention is to provide a method for releasing oocyte maturation regulation by suppressing expression of a gene capable of regulating oocyte maturation in shrimps by the RNA interference method. The present invention provides a method for blocking oocyte maturation inhibition in farmed shrimps to be used as spawners (hereafter, "farmed shrimp"), comprising suppressing the expression of a vitellogenesis-inhibiting hormone (VIH) gene in shrimps by RNA interference using double-stranded RNA (dsRNA) targeting mRNA of the vitellogenesis-inhibiting hormone gene in farmed shrimps.

6 Claims, 9 Drawing Sheets
Specification includes a Sequence Listing.

(56) References Cited

OTHER PUBLICATIONS

Treerattrakooi et al., "Silencing of Gonad-inhibiting Hormone Gene Expression in Penaeus monodon by Feeding with GIH dsRNA-enriched Anemia," *Aquaculture*, 2013, 404-405(2013): 116-121.

* cited by examiner

Fig. 2

```
GGTCGGCAGTCACAGTCGGCCAGCTGCTCTCATACTCTGAACTCTTGACACAGACTGCTCGCCA  : 60
                                                              M
TGACAGCCTTTCGCTTGATGGCCGTGGCCCTGGTGGTCGTGGTCGTGGTGTCGTGCTCGACGACCT  : 120
 T  A  F  R  L  M  A  V  A  L  V  V  V  V  A  C  S  T  T  W
                         Signal peptide
GGGCTCGCTCCGGCCGAGGGGTCGTGTCCCCCCGTGGCCTCCCTCATCAGGGGCCGCAGCC  : 180
 A  R  S  A  E  G  S  S  P  V  A  S  L  I  R  G  R  S  L
                    CPRP
                       ▼     Mature VIH
TCAGCAAGCGAGCAAACTTCGACCCTTCCTGCACGGGCGTCTACGACCGGGAGCTCCTGG  : 240
 S  K  R  A  N  F  D  P  S  C  T  G  V  Y  D  R  E  L  L  G
GGAGGCTGAGCCGCCTCTGCGACGACTGCTACAACGTGTTTCGCGAGCCCAAGGTGGCCA  : 300
 R  L  S  R  L  C  D  D  C  Y  N  V  F  R  E  P  K  V  A  T
CGGAGTGCCAGGAGCAACTGCTTCTACAACCCGGTGTTCGTCCAGTGCCTGGAGTACCTGA  : 360
 E  C  R  S  N  C  F  Y  N  P  V  F  V  Q  C  L  E  Y  L  I
TTCCGGCCGACCTGCACGAGGAGTACCAAGCCCTCGTGCAGACGGGTGGGCAAGTAGGCTC  : 420
 P  A  D  L  H  E  E  Y  Q  A  L  V  Q  T  V  G  K  *
GCTCGACCTGCCACGGCCTCGCGCACTCACGCCAACGGCCGGAAGACACAGAGAG  : 480
GATTTCAGGATTTGTTTCTTGGCTAACTGGTGTATTTCATCGACCTGCTCGGATTTTGAT  : 540
ATGATTCTCATGTCCTAAATTGTGATGAATCTCTAAATGAAGTGTG         : 580
```

Nucleotide sequence: SEQ ID NO: 9
Amino acid sequence: SEQ ID NO: 10

Fig. 5

```
     AGTGCCTTCACCACATCTAAAAGCCGTTGATTTACACGAGCTATGACTGCCTTCCGTATGGTCAATGTTG  :80

M  T  A  F  R  M  V  W  S  M  L  L
                                  Signal peptide                      CPRP
                                       ↓
     GCTTCTTACTGCTGCTGGCTGCGAGCTCGGCGCCTGTCGCCCCGGCGCTCTATCCGCGGCAGGCCTCACCAA  :160
 13  A  S  L  L  L  L  A  A  S  S  A  A  P  A  D  A  L  S  A  P  A  A  G  L  T  K
                                             Mature SGP-C
                    ↓
     ACGGCTCGCTTCGACCCTTCCTGCACCGGCGTCTTCGACCGGCAGCTCTTGCGGAGGGTTGCGTGTGACGACT  :240
 40  R  S  L  F  D  P  S  C  T  G  V  F  D  R  Q  L  L  R  R  V  C  D  D  C GTTTCAACGTATTCAGGGAACCCAACGCCAACGTGTCACTGAATGCAGAAGTAACTGTTACAACAATGAAGTGTTCCGCCAGTGT  :320
 67  F  N  V  F  R  E  P  N  V  S  T  E  C  R  S  N  C  Y  N  N  E  V  F  R  Q  C ATGGAATACCTCCTCCCGCCTCACCTTCATGAAGAACACAGACTAGCTGTCCAGATGGTTCGGAAATAGATTTACGGTTA  :400
 93  M  E  Y  L  L  P  P  H  L  H  E  E  H  R  L  A  V  Q  M  V  G  K  *

AGACGCTGCAACCACCCACTCGCTGACGACAGGAATTCGATGATAGTAAAAGGCACCCTAATTCCACTTATTCTACAGGCATA  :480
     GCACTGAGTCCTCGATCGCTGTAACGATGGTTTCAATGCTGAAGACTATACTGAAGCTGACTTCCACTCT  :560
     AAGAATAAGAATGAAGATGCAGTTGCAGTTGCAGGTGCAGTTGCCACTATGACACAGATTAGTGGGCCACTGATCACAGT  :640
     ATAGAAAATATATAAGGACTATCTGATGAACATGAAGCCAATTTATCAGGAGAAAATGGAGAAAAATATCACTGAAAGAGATTGTTCTTAGGA  :720
     CTCGAGGCTTTAATTAACATTAGAATAGAATAGTTTGATGTTTTAATGTTTAAATTTACGAATAAAGCACTGGCATGC  :800
     TAAAAAAAAAAAAAAAAAAAAAAAAAAAAAAA
```

Nucleotide sequence: SEQ ID NO: 5
Amino acid sequence: SEQ ID NO: 6

Fig. 6

```
TTGCCGTAAACTATGCTTGCCTACCGTACTATGTGGTCAGGCGATAATGGCCTCTTTGCTGCTCGCGGCGTCGTCC  :  80
                    M  L  A  Y  R  T  M  W  S  A  I  M  A  S  L  L  L  L  A  A  S  S
                                                                          ↓ Mature SGP-A
GCTGCCCCGGCCGACGCCTTATCCGCCCCTGCCGGCAGGCCTCACCAAACGCTGGCTATTCGACCCTTCCTGCAGCGGCGT  : 160
 A  A  P  A  D  A  L  S  A  P  A  A  G  L  T  K  R  S  L  F  D  P  S  C  S  G  V CTTCGACCGGCAGCTCTTGCGGAGGCTGCGTCGAGTGTGTGATGACTGTTTCAACGTATTAGGAACCCAACGTAGCTA  : 240
 F  D  R  Q  L  L  R  R  L  R  R  V  C  D  D  C  F  N  V  F  R  E  P  N  V  A  I TTTGATTGCAGGGAGAACTGTTACAACAACGAAGTGTTCCGCCAGTGCATGGCATACGTCGTTCCCGCAAACCTCCACGAC  : 320
 D  C  R  E  N  C  Y  N  N  E  V  F  R  Q  C  M  A  Y  V  V  P  A  N  L  H  D GAACACAGGCAAGCCGTGCAGATGGTCGGCAAGTAAACTACTTC
 E  H  R  Q  A  V  Q  M  V  G  K  *
```

Nucleotide sequence: SEQ ID NO: 1
Amino acid sequence: SEQ ID NO: 2

Fig. 7

```
GAAGAGCCTCGAAGTCGCCGTCTCTCCTCCCGATTCGAGTCGACTGGTGTGCGTTCA  : 80
                                 M  I  G  V  R  L  V  R  S

GCTGTCCTGGTATCCCTGCTGCTGGTAGTGTTCCCGGCCTCTGTCCTGGACGGAAATGAAATCCCTCCGTCCCT  :160
 A  V  L  V  S  L  L  L  V  F  P  A  S  V  L  D  G  N  E  I  P  P  S  L

↓ Mature SGP-B
GCCTTCCTCCTCAGAATCCTCTGCCTGAGCCCAGAGACCCCAGAGCCAAACAAGCGCAGCATATCCTTCGACT  :240
 P  S  S  E  S  S  P  A  T  P  L  A  G  A  Q  T  A  N  K  R  S  I  S  F  D  S CGTGCACGGGGCCTCTACGACCGCGAACTCCTTGTAAGGCTCGACCGCGTGTGCGAAGACTGCTACAACCTGTACCGCGAC  :320
 C  T  G  V  Y  D  R  E  L  L  V  R  L  D  R  V  C  E  D  C  Y  N  L  Y  R  D ACCGACGTGGCGGTCGAATGCAGGAGCAACTGTTTCCACAACGAGGTATTCCTGTACTGCGTCGACTACATGTACCGGCC  :400
 T  D  V  A  V  E  C  R  S  N  C  F  H  N  E  V  F  L  Y  C  V  D  Y  M  Y  R  P TCGCCAAAGGAACCAGTACCGGGCCGCCCTGCAGAGGCTCGGCAAGTAGG
 R  Q  R  N  Q  Y  R  A  A  L  Q  R  L  G  K  *

Nucleotide sequence: SEQ ID NO: 3
Amino acid sequence: SEQ ID NO: 4
```

Fig. 8

```
GAAAGGACCTCGTTGCAATTGAGTATTTCGAGTTTTCGCGTCATTTACAATGTACTTCAATACATGCTGTCTGCGGCCCT  : 80
                                            M   V   L   Q   Y   M   L   S   A   A   L

GCTGGTGCTCGCGGCCTCGTCCTCGCCCGCCGCCCGCTCCCTCGACGCGGCCCCTTCGTCTGCGTCCTCAGGAAGCC     :160
 L   V   L   A   A   S   S   P   A   A   A   R   S   L   D   A   A   P   S   S

↓ Mature SGP-F
ACAGCCCTCAGCAAGCGCTCCCTCTTCGACCCGGCGTGCACCGGCATCTACGACCGGCAGCTGCTGGGCAAGCTGGGGCGC :240
 S   S   L   S   K   R   S   L   F   D   P   A   C   T   G   I   Y   D   R   Q   L   L   G   K   L   G   R CTGTGCGACGACTGCTACAACGTGTTCCGGGAGCCCAAGGTGGCCACGGGATGCAGGAGTAACTGCTACTACAACCTCAT  :320
 L   C   D   D   C   Y   N   V   F   R   E   P   K   V   A   T   G   C   R   S   N   C   Y   Y   N   L   I CTTCCTCGACTGCCTCGAGTACCTGATCCCGAGCCACCTTCAGGAGGAGCACATGTCGGCCCTGCAGACCGTCGGCAAAT  :400
 F   L   D   C   L   E   Y   L   I   P   S   H   L   Q   E   E   H   M   S   A   L   Q   T   V   G   K   *

AAAG

Nucleotide sequence: SEQ ID NO: 7
Amino acid sequence: SEQ ID NO: 8
```

METHOD OF RELEASING THE SUPPRESSION OF EGG MATURATION IN ECONOMICALLY-IMPORTANT PRAWN/SHRIMP SPECIES

CROSS-REFERENCE TO RELATED APPLICATIONS

This application is the U.S. National Stage of PCT/JP2017/038853, filed Oct. 27, 2017, which claims priority to JP 2016-214411, filed Nov. 1, 2016.

The instant application contains a Sequence Listing which has been submitted in ASCII format via EFS-WEB and is hereby incorporated by reference in its entirety. Said ASCII copy, created on Mar. 12, 2019, is named sequence.txt and is 23 KB.

TECHNICAL FIELD

The present invention relates to a method for regulating inherent biological functions in vivo in shrimps using a molecular biology technique. Specifically, the present invention relates to a method for releasing oocyte maturation inhibition by suppressing expression of a gene capable of regulating oocyte maturation in shrimps.

BACKGROUND ART

Currently, about 200 billion young shrimps are produced worldwide to support 3.5 million tons of annual whiteleg shrimp (*Litopenaeus vannaniei*) farming production, and 800,000 shrimps are produced as parent shrimps and exported even only by Hawaii in the United States. It is difficult to artificially mature Penaeidae shrimps including whiteleg shrimps. Under the present circumstances, eyestalk ablation is performed to promote maturation. However, eyestalk ablation is problematic because the maturity success rate is low. Besides, it is also getting criticized for animal cruelty because one of eyestalks of is removed from a shrimp by ablation. It is an urgent task to develop maturation promotion technology to replace eyestalk ablation and realize planned and efficient production of young shrimps.

RNA interference (RNAi) is a phenomenon in which mRNA is cleaved in a sequence-specific manner by double-stranded RNA (dsRNA) such that gene expression is suppressed. It has been reported that RNAi is a form of defense common in organisms at the nucleic acid level (see Non Patent Literature 1). In RNAi, when dsRNA is processed by the action of Dicer, siRNA (short interfering RNA) is formed, and siRNA serves as guide RNA to recognize a target sequence and cleave the target mRNA, thereby suppressing gene expression.

At present, in order to artificially allow adult shrimps to mature and spawn in a hatchery or the like, there is no alternative to eyestalk ablation. However, some research cases aimed at suppressing vitellogenesis-inhibiting hormone (VIH) expression in shrimps such as *Penaeus monodon* using the RNA interference method have been recently reported (see Non Patent Literature 1, 2, and 3). In addition, there are patent applications stating that it is possible to promote maturation in the same way (see Patent Literature 1).

CITATION LIST

Patent Literature

Patent Literature 1: U.S. Patent Application Publication No. US2015/0099702

Non Patent Literature

Non Patent Literature 1: Tiu and Chan, 2007, FEBS Journal, 274: 4385-4395
Non Patent Literature 2: Treerattrakool et al., 2008, FEBS Journal, 275: 970-980
Non Patent Literature 3: Treerattrakool et al., 2013, Aquaculture, 404-405: 116-121

SUMMARY OF INVENTION

Technical Problem

An objective of the present invention is to provide a method for releasing oocyte maturation inhibition, by suppressing the expression of a gene capable of regulating oocyte maturation in shrimps based on RNA interference.

Solution to Problem

The present inventors made intensive studies to arrive at a method for regulating oocyte maturation in shrimps, comprising suppressing the expression of a gene capable of regulating oocyte maturation in shrimps using dsRNA that binds to mRNA of the gene capable of regulating oocyte maturation in shrimps based on the principle of RNA interference. It was the first step to enabling efficient maturation regulation based on biochemical research, thereby blocking the expression of a hormone gene inhibiting in vivo maturation. Accordingly, the present inventors found that it is possible to efficiently suppress the expression of a gene capable of regulating oocyte maturation in shrimps using dsRNA as described above, thereby releasing oocyte maturation inhibition.

Further, the present inventors found that a plurality of genes are involved in oocyte maturation inhibition, and the use of a mixture of a plurality of dsRNAs each capable of suppressing the expression of the relevant gene makes it possible to suppress the expression of each gene capable of regulating oocyte maturation with improved efficiency. This has led to the completion of the present invention.

Specifically, the present invention is described as follows.
[1] A method for releasing oocyte maturation inhibition in farmed shrimps to be used as spawners (hereafter, "farmed shrimp"), comprising suppressing the expression of a vitellogenesis-inhibiting hormone (VIH) gene in shrimps by RNA interference using double-stranded RNA (dsRNA) targeting mRNA of the vitellogenesis-inhibiting hormone gene in farmed shrimps.
[2] The method according to [1], wherein the farmed shrimps are shrimps belonging to the family Penaeidae.
[3] The method according to [2], wherein the farmed shrimps are adult or subadult whiteleg or kuruma shrimps.
[4] The method according to any one of [1] to [3], wherein the double-stranded RNA (dsRNA) targeting mRNA of the vitellogenesis-inhibiting hormone (VIH) gene has a nucleotide sequence identical to a part of the nucleotide sequence of the VIH gene, and wherein a sense strand capable of hybridizing with the gene and an antisense strand having a nucleotide sequence complementary to the nucleotide sequence of the sense strand are bound to each other in the dsRNA.

[5] The method according to any one of [1] to [4], wherein the vitellogenesis-inhibiting hormone gene is one or more types of genes selected from the group consisting of whiteleg shrimp sinus gland peptides SGP-A, SGP-B, SGP-C, SGP-F, and SGP-G.

[6] The method according to any one of [1] to [5], comprising using one or more types of double-stranded RNAs (dsRNAs) selected from the group consisting of: double-stranded RNA (dsRNA) having a sense strand consisting of the nucleotide sequence set forth in SEQ ID NO: 28 for targeting the SGP-A gene; double-stranded RNA (dsRNA) having a sense strand consisting of the nucleotide sequence set forth in SEQ ID NO: 30 for targeting the SGP-B gene; double-stranded RNA (dsRNA) having a sense strand consisting of the nucleotide sequence set forth in SEQ ID NO: 33 for targeting the SGP-C gene; a double-stranded RNA (dsRNA) having a sense strand consisting of the nucleotide sequence set forth in SEQ ID NO: 36 for targeting the SGP-F gene; and a double-stranded RNA (dsRNA) having a sense strand consisting of the nucleotide sequence set forth in SEQ ID NO: 39 for targeting the SGP-G gene.

[7] A composition for releasing oocyte maturation inhibition in farmed shrimps by suppressing the expression of a vitellogenesis-inhibiting hormone (VIH) gene in shrimps, comprising double-stranded RNA (dsRNA) targeting mRNA of a vitellogenesis-inhibiting hormone (VIH) gene, wherein the dsRNA has a nucleotide sequence identical to a part of the nucleotide sequence of the VIH gene, and wherein a sense strand capable of hybridizing with the gene and an antisense strand having a nucleotide sequence complementary to the nucleotide sequence of the sense strand are bound to each other in the dsRNA.

[8] The composition according to [7], wherein the farmed shrimps are shrimps belonging to the family Penaeidae.

[9] The composition according to [8], wherein the farmed shrimps are adult or subadult whiteleg or kuruma shrimps.

[10] The composition according to any one of [7] to [9], wherein the vitellogenesis-inhibiting hormone gene is one or more types of genes selected from the group consisting of whiteleg shrimp sinus gland peptides SGP-A, SGP-B, SGP-C, SGP-F, and SGP-G.

[11] The composition according to any one of [7] to [10], comprising one or more types of double-stranded RNAs (dsRNAs) selected from the group consisting of: double-stranded RNA (dsRNA) having a sense strand consisting of the nucleotide sequence set forth in SEQ ID NO: 28 for targeting the SGP-A gene; double-stranded RNA (dsRNA) having a sense strand consisting of the nucleotide sequence set forth in SEQ ID NO: 30 for targeting the SGP-B gene; double-stranded RNA (dsRNA) having a sense strand consisting of the nucleotide sequence set forth in SEQ ID NO: 33 for targeting the SGP-C gene; a double-stranded RNA (dsRNA) having a sense strand consisting of the nucleotide sequence set forth in SEQ ID NO: 36 for targeting the SGP-F gene; and a double-stranded RNA (dsRNA) having a sense strand consisting of the nucleotide sequence set forth in SEQ ID NO: 39 for targeting the SGP-G gene.

The present description includes part or all of the contents as disclosed in the description and/or drawings of Japanese Patent Application No. 2016-214411, which is a priority document of the present application.

Advantageous Effects of Invention

The use of double stranded RNAs (dsRNAs) according to the present invention makes it possible to suppress the expression of genes responsible for inhibiting oocyte maturation in shrimps based on the principle of RNA interference, thereby releasing oocyte maturation inhibition. As described above, by promoting oocyte maturation in shrimps in which oocyte maturation is successfully inhibited, it is possible to produce young shrimps in a planned and efficient manner.

The use of the double-stranded RNAs (dsRNAs) according to the present invention makes it possible to completely knockdown gene expression in all individuals in 10 days. This state can be maintained for at least 30 days. In addition, in the case of using dsRNAs according to the present invention, the gene expression knockdown rate is from 76.9% to 99.9%. Meanwhile, according to the results obtained by the other groups based on RNA interference disclosed in, for example, Feijo et al. (2016), Mar Biotechnol. 18:117-123, the gene expression knockdown rate is merely from 64% to 73% after administration.

BRIEF DESCRIPTION OF DRAWINGS

FIG. 2 depicts the nucleotide sequence and deduced amino acid sequence of VIH (SGP-G) cDNA in whiteleg shrimps. Each arrow (▼) represents a putative cleavage site, and each dsRNA primer site is double-underlined. The number of nucleotides is indicated on the right.

FIG. 5 depicts the nucleotide sequence and deduced amino acid sequence of SGP-C cDNA in whiteleg shrimps. Each arrow (↓) represents a putative cleavage site, and each dsRNA primer site is double-underlined. The number of nucleotides is indicated on the right, the number of amino acids is indicated on the left.

FIG. 6 depicts the nucleotide sequence and deduced amino acid sequence of SGP-A eDNA in whiteleg shrimps. Each arrow (↓) represents a putative cleavage site, each dsRNA primer site is double-underlined, and each dsRNA site to be synthesized is written in bold. The number of nucleotides is indicated on the right.

FIG. 7 depicts the nucleotide sequence and deduced amino acid sequence of SGP-B cDNA in whiteleg shrimps. Each arrow (↓) represents a deduced cleavage site, each dsRNA primer site is double-underlined, and each dsRNA site to be synthesized is written in bold. The number of nucleotide sequences is shown on the right side. The underlined portion indicates that a deduced amino acid sequence from cDNA differs from the reported peptide sequence.

FIG. 8 depicts the nucleotide sequence and deduced amino acid sequence of SGP-F cDNA in whiteleg shrimps. Each arrow (↓) represents a putative cleavage site, each dsRNA primer site is double-underlined, and each dsRNA site to be synthesized is written in bold. The number of nucleotides is indicated on the right. The underlined portion indicates that a deduced amino acid sequence from cDNA differs from the reported peptide sequence.

DESCRIPTION OF EMBODIMENTS

Figure 1:
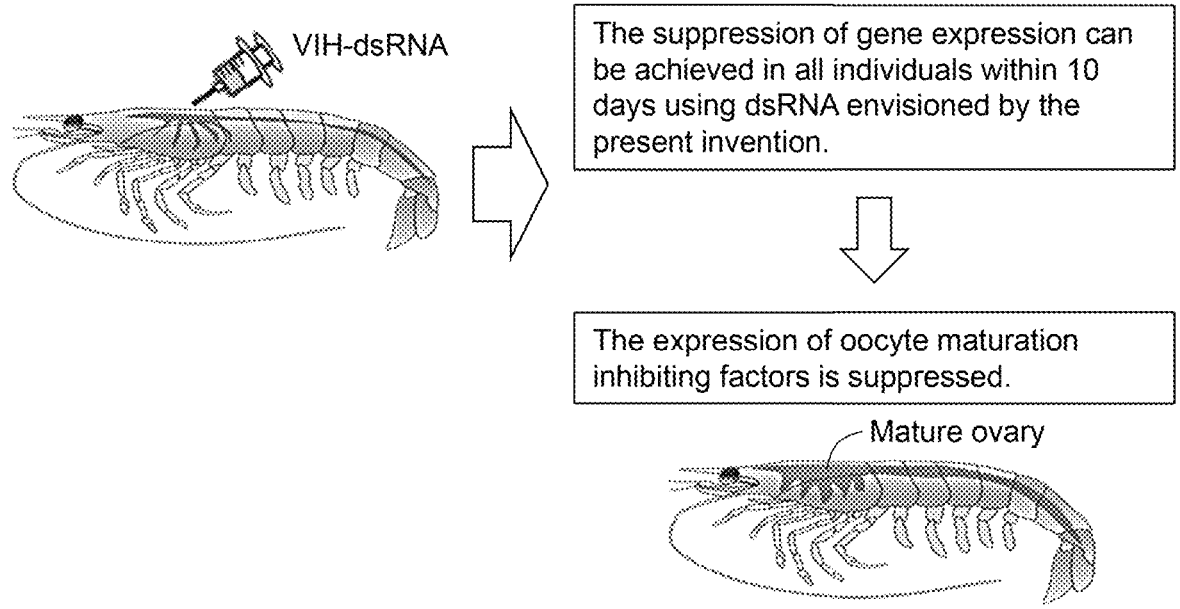
FIG. 1 depicts the concept of the method of the present invention.

The present invention will be described in detail below.

The present invention provides a method for releasing oocyte maturation inhibition, comprising suppressing the expression of a gene capable of regulating oocyte maturation in shrimps based on RNA interference.

Oocyte maturation inhibition occurs in farmed shrimps. Conventionally, eyestalk ablation is performed to promote oocyte maturation. According to the present invention, oocyte maturation inhibition is released by suppressing the expression of a gene capable of regulating oocyte maturation in farmed shrimps.

Shrimps in which oocyte maturation inhibition is released by the method of the present invention are shrimps belonging to the family Penaeidae, including kuruma shrimps (*Penaeus japonicus*), whiteleg shrimps (*Litopenaeus vannamei*), Chinese white shrimps (*Penaeus chinensis*), green tiger shrimps (*Penaeus semisulcatus*), giant tiger shrimps (*Penaeus monodon*), and western king shrimps (*Melicertus latisulcatus*). Of these, whiteleg shrimps or kuruma shrimps, which are mass-produced as edible shrimps, are preferable. In addition, either adult shrimps or subadult shrimps may be used. Here, subadult shrimps are defined as having body weights of 10 g to less than 25 g, and adult shrimps are defined as having body weights of 35 g or more.

Genes inhibiting oocyte maturation in shrimps, which are treated by the method of the present invention so as to suppress the expression of the genes, are genes belonging to the crustacean hyperglycemic hormone (CHH) family. Examples of genes belonging to the CHH family include crustacean hyperglycemic hormone (CHH) genes, vitellogenesis-inhibiting hormone (VIH) genes, and molt-inhibiting hormone (MIH) genes. The term "vitellogenesis-inhibiting hormone" (VIH) is also referred to as "gonad-inhibiting hormone."

According to the present invention, the expression of vitellogenesis-inhibiting hormone (VIH) genes belonging to the crustacean hyperglycemic hormone (CHH) family is suppressed. Examples of vitellogenesis-inhibiting hormone (VIH) genes include sinus gland peptide (SGP) genes. There are seven sinus gland peptides which are SGP-A to SGP-G. In the present invention, by suppressing the expression of one or more types of genes of five sinus gland peptides referred to as SGP-A, AGP-B, SGP-C, SGP-F, and SGP-G, it is possible to suppress the expression of vitellogenesis-inhibiting hormones so as to facilitate yolk protein production for oocyte maturation, thereby regulating oocyte maturation.

As described below, the nucleotide sequences of the genes and the amino acid sequences of peptides encoded by the genes are set forth in SEQ ID NOS: 1 to 10.

SEQ ID NO: 1 SGP-A Nucleotide sequence
SEQ ID NO: 2 SGP-A Amino acid sequence
SEQ ID NO: 3 SGP-13 Nucleotide sequence
SEQ ID NO: 4 SGP-B Amino acid sequence
SEQ ID NO: 5 SGP-C Nucleotide sequence
SEQ ID NO: 6 SGP-C Amino acid sequence
SEQ ID NO: 7 SGP-F Nucleotide sequence
SEQ ID NO: 8 SGP-F Amino acid sequence
SEQ ID NO: 9 SGP-G Nucleotide sequence
SEQ ID NO: 10 SGP-G Amino acid sequence In addition, the nucleotide sequence and amino acid sequence of SGP-A are depicted in FIG. 6, the nucleotide sequence and amino acid sequence of SGP-B are depicted in FIG. 7, the nucleotide sequence and amino acid sequence of SGP-C are depicted in FIG. 5, the nucleotide sequence and amino acid sequence of SGP-F are depicted in FIG. 8, and the nucleotide sequence and amino acid sequence of SGP-G are depicted in FIG. 2.

In order to suppress the expression of any of the above genes, double stranded RNA (dsRNA) consisting of double strands targeting mRNA for the gene can be used. dsRNA causes suppression (silencing) of the expression of a target gene by RNA interference. One of strands of such dsRNA has a nucleotide sequence identical to a part of the nucleotide sequence of the relevant gene, which is a sense strand that can hybridize with the gene. The other strand is an antisense strand having a nucleotide sequence complementary to the nucleotide sequence of the sense strand. The sense strand and the antisense strand binds to each other complementarily, thereby forming dsRNA. Note that the sense strand and the antisense strand are not necessarily exactly complementary to each other. As long as they bind to each other complementarily, there may be one or more mismatches, for example, 1 to 10 mismatches, preferably 1 to 5 mismatches, more preferably 1 to 3 mismatches, and particularly preferably 2 or 1 mismatch. Target sequences in the above sinus gland peptide genes may be either coding regions or non-coding regions. Each target sequence may comprise both a coding region and a non-coding region.

According to the present invention, dsRNA comprises small hairpin RNA (shRNA) and small interfering RNA (siRNA). shRNA has a stem loop structure containing a double-stranded portion in which a sense strand and an antisense strand are bound to each other via a loop sequence. In shRNA, the 3' end of the sense strand and the 5' end of the antisense strand are bound to each other via a loop (hairpin loop sequence). Examples of such hairpin loop sequence include, but are not limited, a sequence comprising 5 to 12 nucleotides starting with UU, for example, UUCAAGAGA. dsRNA and shRNA are treated by in vivo processing carried out by Dicer, thereby forming siRNA. In addition, dsRNA may form miRNA. According to the present invention, in a case in which dsRNA having a length of 30 nucleotides or more is provided, the dsRNA is treated by processing due to the action of an RNaseIII-like enzyme called "Dicer" such that an siRNA molecule comprising 21 to 27 nucleotides and having an overhang comprising two nucleotides at the 3' end can be formed.

The number of nucleotides of dsRNA is, but is not limited to, 50 to 800 nucleotides, preferably 100 to 500 nucleotides, and more preferably 100 to 300 nucleotides.

Examples of a sense strand capable of hybridizing with a target sequence of a sinus gland peptide gene of dsRNA to suppress the expression of the sinus gland peptide gene include a sense strand having an RNA sequence comprising a nucleotide sequence which is a partial sequence of any of the nucleotide sequence of the SGP-A gene set forth in SEQ ID NO: 1, the nucleotide sequence of the SGP-B gene set forth in SEQ ID NO: 3, the nucleotide sequence of the SGP-C gene set forth in SEQ ID NO: 5, the nucleotide sequence of the SGP-F gene set forth in SEQ ID NO: 7, and the nucleotide sequence of the SGP-G gene set forth in SEQ ID NO: 9, in which thymine has been substituted with uracil in the gene sequence.

Specifically, for example, it is possible to use one or more types of double-stranded RNAs (dsRNAs) selected from the group consisting of: double-stranded RNA (dsRNA) having a sense strand comprising the nucleotide sequence set forth in SEQ ID NO: 28 for targeting the SGP-A gene; double-stranded RNA (dsRNA) having a sense strand comprising the nucleotide sequence set forth in SEQ ID NO: 30 for targeting the SGP-B gene; double-stranded RNA (dsRNA) having a sense strand comprising the nucleotide sequence set forth in SEQ ID NO: 33 for targeting the SGP-C gene; a double-stranded RNA (dsRNA) having a sense strand comprising the nucleotide sequence set forth in SEQ ID NO: 36 for targeting the SGP-F gene; and a double-stranded RNA (dsRNA) having a sense strand comprising the nucleotide sequence set forth in SEQ ID NO: 39 for targeting the SGP-G gene. Antisense strands comprising sequences complementary to these sense strands hybridize to the sense strands, thereby forming dsRNAs. The above sense strands may be produced using dsRNA primers. A primer for double-stranded RNA (dsRNA) comprising the nucleotide sequence set forth in SEQ ID NO: 28 for targeting the SGP-A gene may be a primer comprising the nucleotide sequence set forth in SEQ ID NO: 27. A primer for double-stranded RNA (dsRNA) comprising the nucleotide sequence set forth in SEQ ID NO: 30 for targeting the SGP-B gene may be a primer comprising the nucleotide sequence set forth in SEQ ID NO: 29. Primers for double-stranded RNA (dsRNA) comprising the nucleotide sequence set forth in SEQ ID NO: 33 for targeting the SGP-C gene may be a primer comprising the nucleotide sequence set forth in SEQ ID NO: 31 and a primer comprising the nucleotide sequence set forth in SEQ ID NO: 32. Primers for double-stranded RNA (dsRNA) comprising the nucleotide sequence set forth in SEQ ID NO: 36 for targeting the SUP-F gene may be a primer comprising the nucleotide sequence set forth in SEQ ID NO: 34 and a primer comprising the nucleotide sequence set forth in SEQ ID NO: 35. Primers for double-stranded RNA (dsRNA) comprising the nucleotide sequence set forth in SEQ ID NO: 39 for targeting SGP-G gene may be a primer comprising the nucleotide sequence set forth in SEQ ID NO: 37 and a primer comprising the nucleotide sequence set forth in SEQ ID NO: 38.

A sense strand that constitutes dsRNA according to the present invention is desirably identical to the nucleotide sequence of a sinus gland peptide gene, which, however, may be a substantially identical sequence. In other words, as long as the sense strand of dsRNA hybridizes with the mRNA sequence of a sinus gland peptide as an actual target, there may be mismatches due to deletion, substitution, or addition of one or more nucleotides, for example, 1 to 10 nucleotides, preferably 1 to 5 nucleotides, and more preferably 1 to 3 nucleotides or 2 or 1 nucleotide.

In order to release oocyte maturation inhibition in shrimps, the expression of at least one type of the above-described sinus gland peptide genes, preferably a plurality of the genes, for example, two, three, four, or five types of the genes, is suppressed. In a case in which the expression of two or more types of the genes is suppressed, it is possible to release oocyte maturation inhibition with improved efficiency. In order to suppress the expression of two or more types of the genes, a plurality of dsRNAs each capable of suppressing the expression of the relevant gene can be used.

A sense strand or an antisense strand that constitutes a dsRNA molecule may have an overhang at the 3' end thereof. The type and number of nucleotides of such overhang are not limited. For example, a sequence comprising 1 to 5 nucleotides, preferably 1 to 3 nucleotides, and more preferably 1 or 2 nucleotides may be used. Specific examples include TTT, UU, and TT. The term "overhang" used herein refers to nucleotides which are added to the end of one strand of a dsRNA molecule and do not include nucleotides that can complementarily bind to nucleotides at the corresponding positions of the other strand.

According to the present invention, dsRNA can be synthesized via chemical synthesis or in vitro synthesis in a transcription system using promoters and RNA polymerases. For example, in the case of chemical synthesis, self-complementary single-stranded RNA having a sequence and another sequence that is a reverse sequence complementary thereto is synthesized, thereby allowing the sequences to bind to each other to form a self-complementary portion. Annealing of a sense strand and an antisense strand of the synthesized dsRNA can be carried out by an ordinary method known to those skilled in the art.

In addition, in a case in which dsRNA is synthesized using a promoter and an RNA polymerase, template DNA having a structure, in which a sense strand and an antisense strand are bound to each other via a loop downstream of the promoter, is synthesized so as to transcribe RNA using the RNA polymerase. In the case of in vitro production, a T7 promoter, a T3 promoter, or the like can be used. In addition, in a case in which template DNA of dsRNA is introduced into a vector and the vector is administered in vivo to a shrimp so as to synthesize dsRNA in vivo according to the present invention, a PolIII promoters such as a H1 promoter or a U6 promoter can be used. In a case in which a vector is used, a plasmid vector, a viral vector, or the like can be used. Examples of a plasmid vector that can be used include pSUPER vectors and pBAsi vectors. Examples of a viral vector that can be used include adenovirus vectors, lentiviral vectors, and retroviral vectors.

The present invention also encompasses vectors capable of expressing the above-described dsRNA molecules.

According to the present invention, dsRNA can cleave mRNA of a sinus gland peptide gene in a sequence-specific manner, thereby inducing RNA interference (RNAi) for suppressing the expression of the sinus gland peptide gene so as to suppress the expression of the sinus gland peptide gene.

In order to suppress the expression of a gene capable of regulating oocyte maturation in shrimps using dsRNA according to the present invention so as to release oocyte maturation inhibition, dsRNA of the present invention can be administered in vivo to shrimps. Administration can be carried out by the oral route as well as injectable or parenteral routes such as intravenous, intramuscular, subcutaneous and intraperitoneal routes. For example, dsRNA can be intraperitoneally injected. In such case, it is preferable to use a thin insulin needle of about 30 G to 33 G. It is also possible to administer dsRNA by mixing the dsRNA with feed and allow shrimps to ingest the feed according to the present invention.

According to the present invention, dsRNA can be prepared with a pharmacologically acceptable carrier, diluent, or excipient for use. Examples of such carrier include physiological saline, phosphate buffered saline, a phosphate buffered saline glucose solution, and buffered saline. In a case in which dsRNA is prepared with a carrier, the content of dsRNA according to the present invention may be appropriately determined depending on a preparation, and it is preferably 0.001% to 1% by weight, which may differ variously depending on a preparation. According to the present invention, 0.0001 to 1 mg of dsRNA can be administered to shrimps once or in divided amounts for several times a day. In addition, the dsRNA molecular weight per administration unit is 1 nM to 100 µM, preferably 10 nM to 50 µM, and more preferably 100 nM to 20 µM.

According to the present invention, suppression (silencing) of the expression of a target gene by RNA interference also includes a case in which when the expression of a gene is determined based on the expression level of mRNA or protein of the gene, the expression is suppressed not only at a rate of 100% but, also at a rate of 75% or more, 50% or more, or 20% or more as compared with a case in which siRNA according to the present invention is not introduced. The degree of suppression of gene expression may be determined by comparing the production of mRNA or protein of the gene before and after introduction of siRNA. In the case of mRNA, measurement can be carried out by northern hybridization, RT-PCR, in situ hybridization, or the like. In the case of a protein, measurement can be carried out by a conventional method such as western blotting or ELISA.

Oocyte maturation inhibition can be released by suppressing the expression of a gene capable of regulating oocyte maturation in shrimps using dsRNA according to the present invention. In other words, the present invention encompasses a method for releasing oocyte maturation inhibition in shrimps by administering dsRNA according to the present invention into shrimps, thereby suppressing the expression of a gene capable of regulating oocyte maturation in shrimps. The method is also referred to as a method for producing shrimps in which oocyte maturation inhibition is released by administering dsRNA according to the present invention into shrimps, thereby suppressing the expression of a gene capable of regulating oocyte maturation in shrimps.

In a case in which dsRNA according to the present invention is administered to shrimps, it is possible to completely suppress the expression of a gene capable of regulating oocyte maturation within several days to more than ten days. The state of suppressing gene expression can be maintained for 10 to 50 days and preferably 30 days. The gene expression suppression rate in the case of using dsRNA according to the present invention is from 76.6% to 99.9%.

As described above, it is possible to produce artificially matured shrimps by promoting oocyte maturation in shrimps which are free from oocyte maturation inhibition. Young shrimps can be produced in a planned and efficient manner from such shrimps.

EXAMPLES

The present invention will be specifically described by the Examples described below, but the present invention is not limited by these Examples.

Example 1: Suppression of the Expression of the Vitellogenesis-Inhibiting Hormone (VIH; SGP-G) Gene in Whiteleg Female Adult Shrimps 1. Production of the Double-Stranded RNA (Ds-RNA) of Vitellogenesis-Inhibiting Hormone (VIH) Gene Cloning of the VIH gene was carried out based on the sequence (SGP-G gene sequence) reported in Tsutsui et al. (2013), Fish. Sci., 79: 357-365, thereby preparing a plasmid. The prepared plasmid was used as a template, and the mature VIH site was amplified using gene specific primers (T7-VIH-L, T7-VIH-R, see Table 1) bound to a T7 promoter. The resulting product was used as a template to produce VIH-dsRNA using MEGAscript RNAi Kits (FIG. 2). Among the sequences listed in Table 1, the sequence represented by TAATACGACTCACTATAGGG (SEQ ID NO: 20) is the sequence of a T7 promoter.

2. Administration of VIH-dsRNA

Female adult whiteleg shrimp individuals (each having a body weight of 39 g to 70 g) in the intermolt stage (Stage C0-C1) were selected and used in experiments. The produced VIH-dsRNA was dissolved in TE buffer (10 mM Tris-HCl pH 7, 1 mM EDTA) (1 µg/µL) and injected in an amount of 3 µg per body weight (g) (VIH-dsRNA plot). In addition, in order to examine the influence of buffer, TE buffer was injected at the same dose (34) per body weight (g) (TE buffer plot). dsRNA (1 µg/µL) for the green fluorescent protein (GFP) gene, which does not exist in vivo in shrimps, was produced as a negative control, and it was injected in an amount of 3 µg per body weight (g) (GFP-dsRNA plot). Sampling from each experimental plot was conducted on days 10 and 20 after injection so as to examine VIH expression in eyestalks. In addition, in order to set the original in vivo VIH expression level as a standard, non-injected female adult shrimp individuals (initial plot) were also sampled so as to examine the expression of the VIH gene in eyestalks. Note that individuals sampled in each experimental plot were labeled in the order of the experimental plot, date of sampling, and reference number. Specifically, individuals sampled 10 days after injection of TE buffer (TE buffer plot) are simply referred to as TE10-1 to TE10-5, and individuals sampled 20 days after injection are simply referred to as TE20-1 to TE20-5.

3. Gene Expression Level Analysis (Total RNA Extraction, Semiquantitative PCR, Quantitative PCR)

Total RNA was purified from each sampled eyestalk using RNeasy mini kits (Qiagen) and Clean-up kits (Qiagen). In some purified total RNA samples (TE10-3, TE10-4, VIH10-2), a remaining hue was observed. Purified total RNA was reverse-transcribed by High capacity RNA to cDNA kits (Applied Biosystems) to synthesize cDNA. The synthesized cDNA was diluted 4-fold, and the dilution was used as a template so as to examine the expression level of the VIH gene by semiquantitative PCR and quantitative PCR.

Under semiquantitative PCR, in order to examine the expression level of the gene of interest, PCR (denaturation at 94° C. for 2 minutes, followed by 30 cycles of 94° C. for 30 seconds, 62° C. for 30 seconds, and 72° C. for 30 seconds) was performed using specific primers (Liv-SGP-G-F:CGGAGTGCAGGAGCAACTG (SEQ ID NO: 21), Liv-R3:CCTCTCTGTGTCTTCTGGCCGTTGG (SEQ ID NO: 22)) for the VIH gene and TaqMan Fast Universal PCR Master Mix (2× NoAmpErase UNG, Applied Biosystems), thereby analyzing the expression level. In addition, PCR was performed in the same manner using primers (Liv-act-Fw1: CGACCTCACAGACTACCTGATGAAGAT (SEQ ID NO: 23), Liv-act-Rv2:GTGGTCATCTCCTGCTCGAAG (SEQ ID NO: 24)) for amplifying the beta-actin gene (ACTB)

serving as an internal standard gene, followed by relative comparison.

Figure 4:
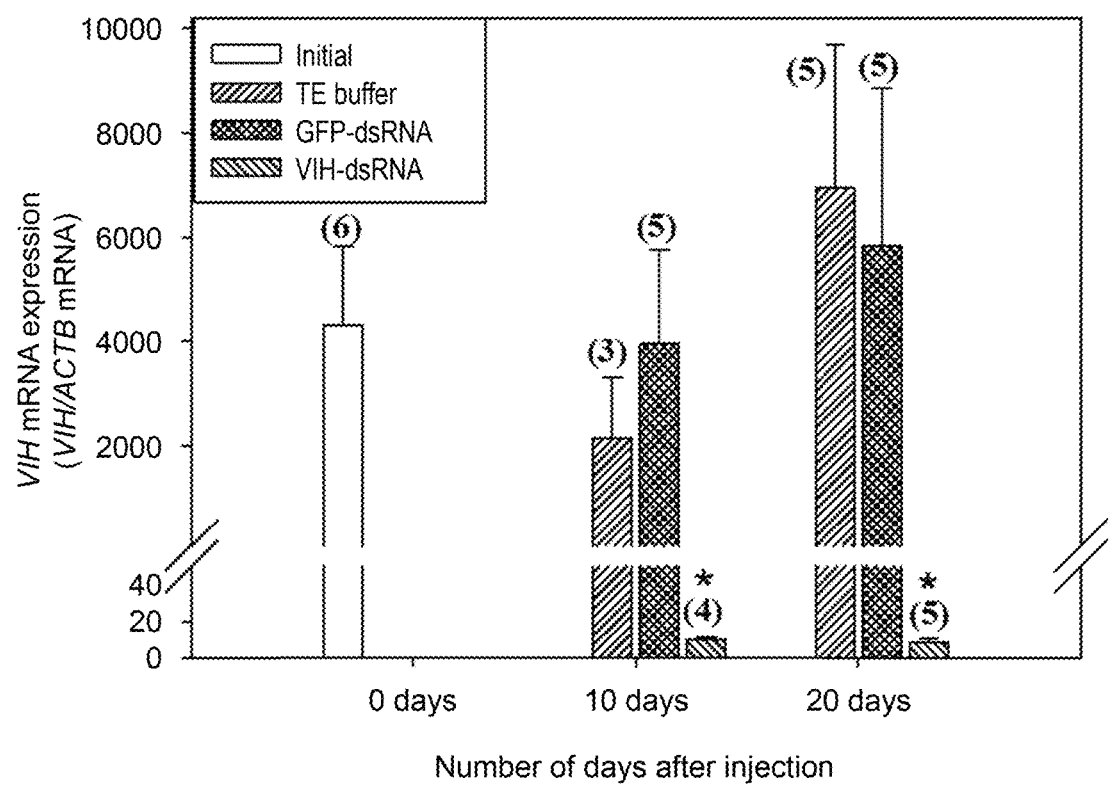
FIG. 4 depicts the measurement results of VIH gene expression in adult shrimp eyestalks by quantitative PCR. (N) represents the number of individuals analyzed, and "*" indicates a significant difference with respect to "Initial" ($P<0.05$).

Under quantitative PCR, in addition to the gene specific primers and kits described above, probes (Liv-SGP-G-Prb: TCTACAACCCCGTGTTCGTCCAGTGC (SEQ ID NO: 25) for VIH and Liv-act-Prb:CGAC-CACCGCCGAGCGAGAAATCGTTCGT (SEQ ID NO: 26) for ACTB) were used so as to perform real-time PCR Further, as depicted in FIG. 4, the results of quantitative PCR showed that the VIH expression level did not significantly vary on both days 10 and 20 in the TE buffer plot and the GFP-dsRNA plot as compared with the initial plot while the VIH expression level was significantly reduced in the VIH-dsRNA plot on both days 10 and 20. As described above, it was demonstrated that VIH gene expression can be suppressed in adult shrimps by injection of VIH-dsRNA.

TABLE I

List of gene specific primers used for RNA interfering

| target gene | Oligo Name | Sequence (5' to 3') |
| --- | --- | --- |
| GFP | T7-EGFP-2L | TAATACGACTCACTATAGGGAGAGCATCGACTTCAAGGAGGAC (SEQ ID NO: 11) |
| GFP | T7-EGFP-2R | TAATACGACTCACTATAGGGAGATGGGTGCTCAGGTAGTGGTT (SEQ ID NO: 12) |
| SGP-G | T7-VIH-L | TAATACGACTCACTATAGGGAGAAAGCGAGCAAACTTCGAC (SEQ ID NO: 13) |
| SGP-G | T7-VIH-R | TAATACGACTCACTATAGGGAGACTACTTGCCCACCGTCTG (SEQ ID NO: 14) |
| SGP-C/ SGP-A | T7_sgpC-L | TAATACGACTCACTATAGGGAGACTCGCTCTTCGACCCTTCC (SEQ ID NO: 15) |
| SGP-C | T1_sgpC-R | TAATACGACTCACTATAGGGAGACTATTTCCCGACCATCTGG (SEQ ID NO: 16) |
| SGP-B | T7-sgpB-L2 | TAATACGACTCACTATAGGGAGACGCAGCATATCCTTCGACTCGT (SEQ ID NO: 17) |
| SGP-F | T7-sgpF-L | TAATACGACTCACTATAGGGAGAAAGCGCTCCCTCTTCGACC (SEQ ID NO: 18) |
| SGP-F | T7-sgpF-R | TAATACGACTCACTATAGGGAGACTTTATTTGCCGACGGTCTGCAGG (SEQ ID NO: 19) |
| | T7 promoter | TAATACGACTCACTATAGGG (SEQ ID NO: 20) |

(7500 Fast Real-Time PCR system, Applied. Biosystems) under the following conditions: denaturation at 95° C. for 2 minutes, followed by 40 cycles of 95° C. for 10 seconds and 62° C. for 30 seconds. The expression level of the VIH gene was obtained as a relative quantitative value calculated based on the expression level of the gene of interest (VIH; SGP-G) with respect to the expression level of the internal standard gene (ACTB).

4. Results

Figure 3:
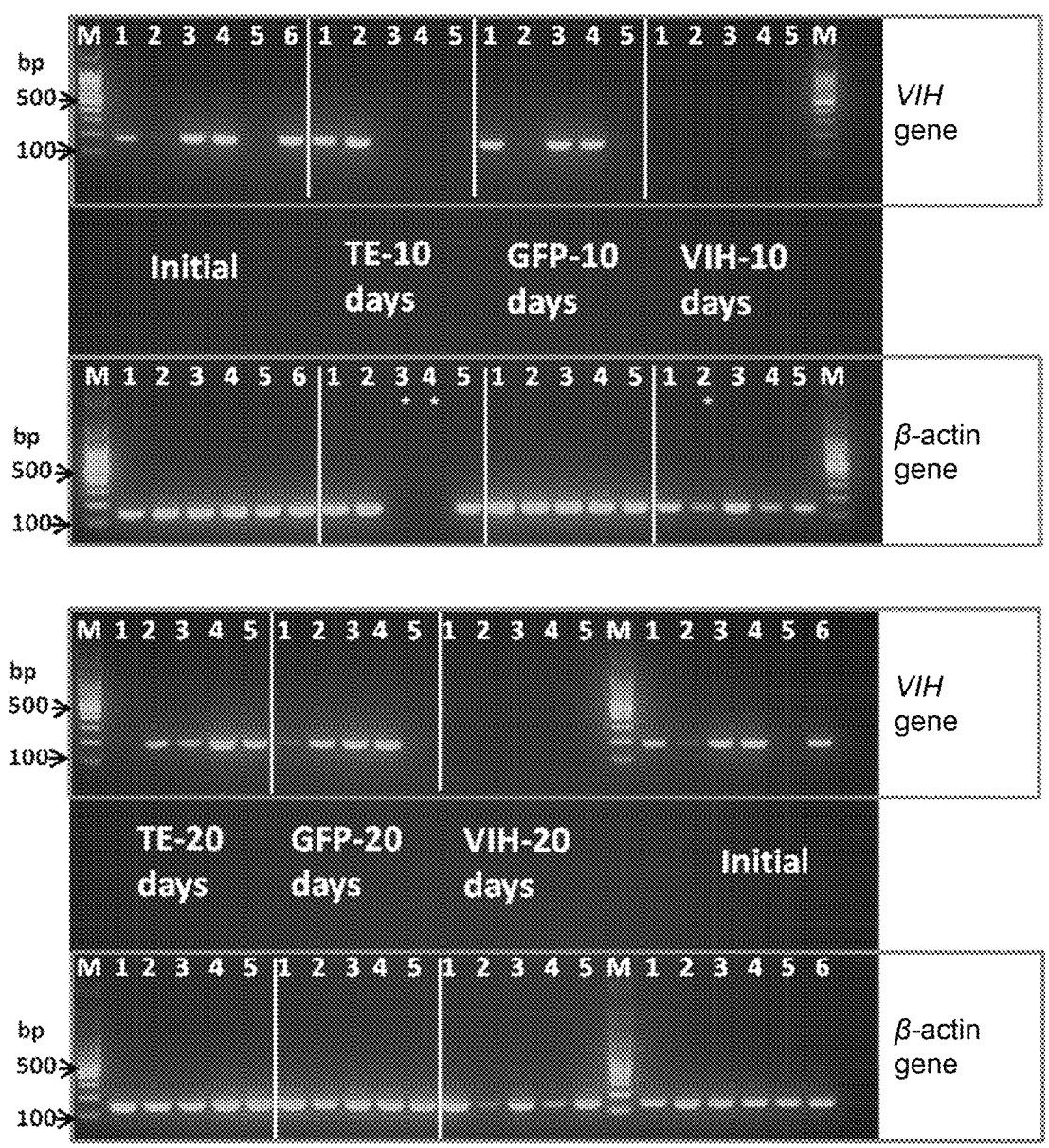
FIG. 3 depicts the measurement results of VIH gene expression in eyestalks by semiquantitative PCR. "Initial" represents a plot without injection, "TE" represents a plot with TE (Tris-EDTA) buffer injection, "GFP" represents a plot with GFP-dsRNA injection, and "VIH" represents a plot with VIH-dsRNA injection.

Among total RNA samples purified from eyestalks, a remaining hue was observed in RNA samples of TE10-3, TE10-4, VIH10-2. After semiquantitative PCR, DNA electrophoresis was performed for confirmation. As a result, the internal standard gene was not amplified in TE10-3 and TE10-4 (FIG. 3), and therefore, the results were excluded from gene expression level analysis. The VIH10-2 sample showed an increase in the internal standard gene. However, as the remaining hue could interfere amplification of VIH, the results were also excluded from gene expression level analysis. After 30 cycles of semiquantitative PCR, the VIH expression was not confirmed in individuals of Initial-2, GFP10-2, 5, TE20-1, and GFP20-5. However, the VIH expression was observed entirely in the initial plot, the TE buffer plot, and the GFP-dsRNA plot. Meanwhile, in the experimental plot of VIH-dsRNA injection, the VIH expression was not observed in all individuals on days 10 and 20.

Example 2: Regulation of VIH Gene Expression in Whiteleg Female Subadult Shrimps 1. Cloning of Sinus Gland Peptides For whiteleg shrimps, seven sinus gland peptides (sinus gland peptides: SGP—A to G) have been identified. It has been reported that among them, six sinus gland peptides (A, B, C, E, F, G) can suppress yolk protein expression (Tsutsui et al., 2007, Mar. Biotechnol., 9:360-369). Since the abundance of SGP-G is largest, SGP-G has been considered to be the major VIH to target in further studies. However, since it has been revealed that the nucleotide sequence of SGP-C is structurally similar to that of the crustacean hyperglycemic hormone (CHH) and SGP-C has an action similar to that of CHH, SGP-C has been determined to have properties of both hormones (Lago-Leston et al., 2007, Aquaculture, 270: 343-357; Liu et al., 2014, Peptides, 53: 115-124). According to the present invention, the VIH expression level can be suppressed via in vivo injection of dsRNAs of not only SGP-G (VIH) but also SGP-C and other similar SGP genes into shrimps. For such reasons, the sequence of SGP-C was obtained from the eyestalk cDNA library, and cloning of cDNAs of SGP-A, SGP-B, and SGP-F was further conducted.

2. Production of dsRNA of Sinus Gland Peptides

As in the case of adult shrimps, a gene fragment of the mature VIH site was amplified by PCR based on the plasmid of the VIH gene, and GFP-dsRNA was produced by MEGAscript RNAi Kits using the amplified product as a template and VIH-dsRNA as a negative control. In addition, as in the case of VIH-dsRNA, in order to synthesize dsRNAs targeting the mature sites of SGP-A, SGP-B, SGP-C, and SGP-F genes, gene fragments were amplified using gene specific primers bound to a T7 promoter and a T7 promoter primer (see Table 1) by PCR using each cloned plasmid as a template by the same method used for VIH-dsRNA, thereby synthesizing dsRNA of each gene. The thus obtained GFP-dsRNA, VIH-dsRNA, and SGP-C-dsRNA were dissolved in TE buffer at a concentration of 3 µg/4 µL for use. Three dsRNAs, namely, SGP-A-dsRNA, SGP-B-dsRNA, and SGP-F-dsRNA, were mixed such that the concentration of each dsRNA was adjusted to 1 ng/4 The resulting product was dissolved in TE buffer to yield a total dsRNA concentration of 3 µg/4 µL for use.

3. Administration of dsRNA

VIH-dsRNA was injected at a concentration of 3 µg per body weight (g) into randomly selected female subadult shrimp individuals (each having a body weight of 15 g to 25 g) only once (VIH-1 plot) or three times at 7-day intervals (VIH-2 plot). SGP-C-dsRNA was injected at a concentration of 3 µg per body weight (g) only once (SGP-C plot). SGP-A-dsRNA, SGP-B-dsRNA, and SGP-F-dsRNA were mixed at equivalent concentrations, and the mixture was injected at a concentration of 3 µg per body weight (g) only once (Mix plot). GFP-dsRNA was injected as a negative control at a concentration of 3 µg per body weight (g) only once (GFP plot). Sampling was conducted on days 10, 20, and 30 after the initial injection, and the VIH expression level in eyestalks was examined.

4. Gene Expression Level Analysis (Total RNA Extraction, Semiquantitative PCR, Quantitative PCR)

Gene expression levels were analyzed in the same manner as in 3 in Example 1.

5. Results

The SGP-C gene cloned from the eyestalk cDNA library was found to encode an amino acid sequence of 115 residues, and its primary structure was composed of a signal peptide (24 residues), CPRP (a CHH precursor-related peptide; 16 residues), and a mature SGP-C (75 residues) (FIG. 5). In addition, cDNAs which were considered to correspond to the SGP-A, SGP-B, and SGP-F genes were also successfully cloned. Each cDNA was compared with the peptide sequence previously extracted from eyestalks. In the case of SGP-A, there was consistency in the putative amino acid sequence of the mature site (FIG. 6), while two amino acid residues were different in SGP-B (FIG. 7) and SGP-F (FIG. 8). These cDNAs were each used as a template for synthesis of the corresponding dsRNA. In FIGS. 2 and 5 to 8, the sequence of each dsRNA primer used for dsRNA production is double-underlined. Each primer was used for producing dsRNA for suppressing the expression of the relevant sinus gland peptide gene. The dsRNA sequence for SGP-G in FIG. 2 is set forth in SEQ ID NO: 39, and the sequences of dsRNA primers for producing dsRNA of SGP-G are set forth in SEQ ID NOS: 37 and 38. The dsRNA sequence for SGP-C in FIG. 5 is set forth in SEQ ID NO: 33, and the sequences of dsRNA primers for producing dsRNA of SGP-C are set forth in SEQ ID NOS: 31 and 32. The dsRNA sequence for SGP-A in FIG. 6 is set forth in SEQ ID NO: 28, and the sequence of a dsRNA primer for producing dsRNA of SGP-A is set forth in SEQ ID NO: 27. The dsRNA sequence for SGP-B in FIG. 7 is set forth in SEQ ID NO: 30, and the sequence of a dsRNA primer for producing dsRNA of SGP-B is set forth in SEQ ID NO: 29. The dsRNA sequence for SGP-F in FIG. 8 is set forth in SEQ ID NO: 36, and the sequences of dsRNA primers for producing dsRNA of SGP-F are set forth in SEQ ID NOS: 34 and 35.

Figure 9:
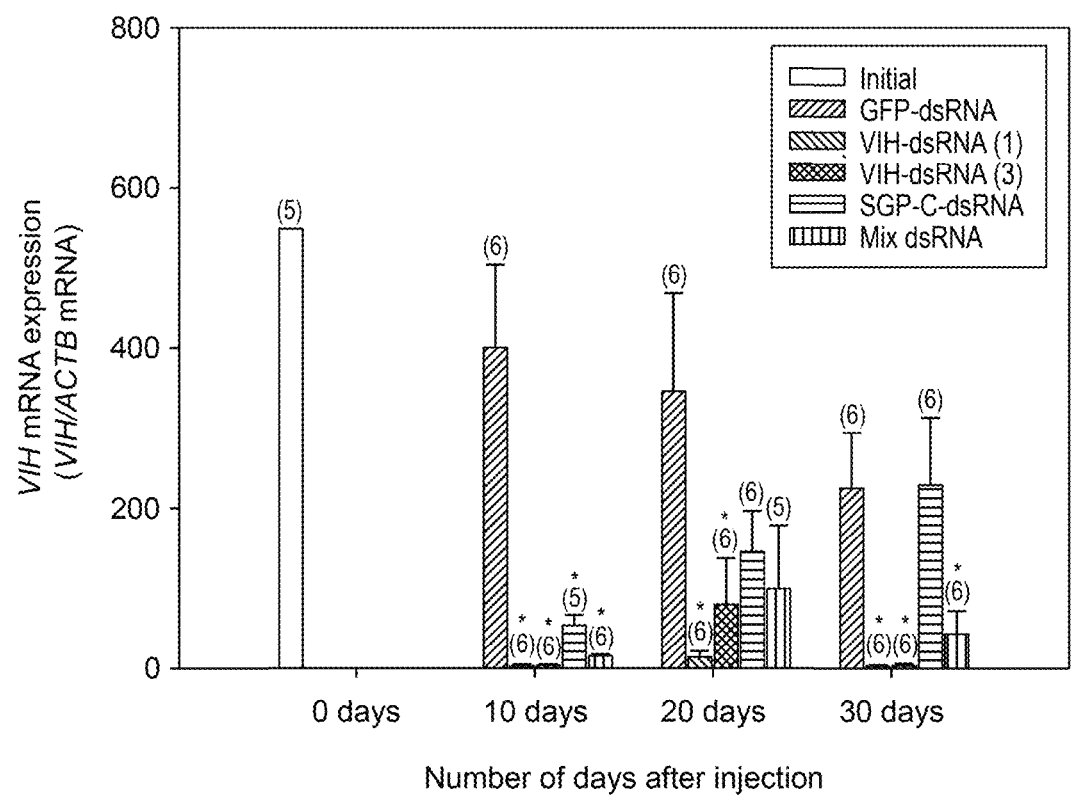
FIG. 9 depicts the measurement results of VIH gene expression in subadult shrimp eyestalks by quantitative PCR. (N) represents the number of individuals analyzed, and "*" indicates a significant difference with respect to "Initial" (P<0.05).

VIH gene expression in eyestalks followed by dsRNA injection was analyzed by quantitative PCR. As a result, with respect to the initial plot (without injection), the GFP plot in which GFP-dsRNA was injected, there was no significant decrease in the VIH expression level on days 10, 20, and 30. However, in the VIH-1 plot (1 injection) and plot (3 injections) in which VIH-dsRNA was injected, there was a significant decrease in the VIH expression level on days 10, 20, and 30 after injection (FIG. 9). In the SGP-C plot in which dsRNA of a similar SGP-C gene was injected, although the VIH expression level significantly declined on day 10 after injection, there was no significant difference as compared with the VIH expression level of the initial plot on days 20 and 30. In addition, in the Mix plot in which the mixture of dsRNAs of the SGP-A, SGP-B, and SGP-F genes was injected, although the VIH expression level significantly declined on days 10 and 30 after injection, there was no significant difference as compared with the VIH expression level of the initial plot on day 20.

As described above, it is possible to remarkably reduce the expression level of the VIH gene using dsRNA of VIH (SGP-G) in subadult shrimps as well. In addition, it is also possible to obtain similar effects using other similar VIH genes.

INDUSTRIAL APPLICABILITY

Shrimps can be produced in a planned and efficient manner using the dsRNAs of the present invention.

Sequence Listing Free Text

SEQ ID NOS: 11-19, 21-27, 29, 31, 32, 34, 35, 37, and 38 for primers

All publications, patents and patent applications cited in the present description are incorporated herein by reference in their entirety.

The invention claimed is:

1. A method for releasing oocyte maturation inhibition in farmed shrimps to be used as spawners, comprising suppressing the expression of a vitellogenesis-inhibiting hormone (VIH) gene in shrimps by RNA interference using double-stranded RNA (dsRNA) targeting mRNA of the vitellogenesis-inhibiting hormone gene in farmed shrimps, wherein the vitellogenesis-inhibiting hormone gene is selected from sinus gland peptides SGP-A, SGP-B, SGP-C, SGP-F, and SGP-G, wherein the dsRNA has a nucleotide sequence identical to a part of the nucleotide sequence of the VIH gene, wherein a sense strand capable of hybridizing with the gene and an antisense strand having a nucleotide sequence complementary to the nucleotide sequence of the sense strand are bound to each other in the dsRNA, and wherein the dsRNA is selected from the group consisting of: double-stranded RNA (dsRNA) having a sense strand consisting of the nucleotide sequence set forth in SEQ ID NO: 28 for targeting the SGP-A gene; double-stranded RNA (dsRNA) having a sense strand consisting of the nucleotide sequence set forth in SEQ ID NO: 30 for targeting the SGP-B gene; double-stranded RNA (dsRNA) having a sense strand consisting of the nucleotide sequence set forth in SEQ ID NO: 33 for targeting the SGP-C gene; a double-stranded RNA (dsRNA) having a sense strand consisting of the nucleotide sequence set forth in SEQ ID NO: 36 for targeting the SGP-F gene; and a double-stranded RNA (dsRNA) having a sense strand consisting of the nucleotide sequence set forth in SEQ ID NO: 39 for targeting the SGP-G gene.

2. The method according to claim 1, wherein the farmed shrimps are shrimps belonging to the family Penaeidae.

3. The method according to claim 2, wherein the farmed shrimps are adult or subadult whiteleg or kuruma shrimps.

4. A composition for releasing oocyte maturation inhibition in farmed shrimps by suppressing the expression of a vitellogenesis-inhibiting hormone (VIH) gene in shrimps, comprising double-stranded RNA (dsRNA) targeting mRNA of a vitellogenesis-inhibiting hormone (VIH) gene selected from sinus gland peptides SGP-A, SGP-B, SGP-C, SGP-F, and SGP-G, wherein the dsRNA has a nucleotide sequence identical to a part of the nucleotide sequence of the VIH gene, and wherein a sense strand capable of hybridizing with the gene and an antisense strand having a nucleotide sequence complementary to the nucleotide sequence of the sense strand are bound to each other in the dsRNA, wherein the dsRNA is selected from the group consisting of: double-stranded RNA (dsRNA) having a sense strand consisting of the nucleotide sequence set forth in SEQ ID NO: 28 for targeting the SGP-A gene; double-stranded RNA (dsRNA) having a sense strand consisting of the nucleotide sequence set forth in SEQ ID NO: 30 for targeting the SGP-B gene; double-stranded RNA (dsRNA) having a sense strand consisting of the nucleotide sequence set forth in SEQ ID NO: 33 for targeting the SGP-C gene; a double-stranded RNA (dsRNA) having a sense strand consisting of the nucleotide sequence set forth in SEQ ID NO: 36 for targeting the SGP-F gene; and a double-stranded RNA (dsRNA) having a sense strand consisting of the nucleotide sequence set forth in SEQ ID NO: 39 for targeting the SGP-G gene.

5. The composition according to claim 4, wherein the farmed shrimps are shrimps belonging to the family Penaeidae.

6. The composition according to claim 5, wherein the farmed shrimps are adult or subadult whiteleg or kuruma shrimps.

* * * * *

SEQUENCE LISTING

<160> NUMBER OF SEQ ID NOS: 39

<210> SEQ ID NO 1
<211> LENGTH: 364
<212> TYPE: DNA

<213> ORGANISM: Litopenaeus vannamei
<220> FEATURE:
<221> NAME/KEY: CDS
<222> LOCATION: (12)..(356)

<400> SEQUENCE: 1

```
ttgcgtaaac t atg ctt gcc tac cgt act atg tgg tca gcg ata atg gcc      50
             Met Leu Ala Tyr Arg Thr Met Trp Ser Ala Ile Met Ala
              1               5                  10 tct ttg ctg ctg ctg ctc gcg gcg tcg tcc gct gcc ccc gcc gac gcc      98
Ser Leu Leu Leu Leu Leu Ala Ala Ser Ser Ala Ala Pro Ala Asp Ala
     15                  20                  25 tta tcc gcc cct gcg gca ggc ctc acc aaa cgc tcg cta ttc gac cct      146
Leu Ser Ala Pro Ala Ala Gly Leu Thr Lys Arg Ser Leu Phe Asp Pro
 30                  35                  40                  45 tcc tgc agc ggc gtc ttc gac cgg cag ctc ttg cgg agg ctg cgt cga      194
Ser Cys Ser Gly Val Phe Asp Arg Gln Leu Leu Arg Arg Leu Arg Arg
                 50                  55                  60 gtg tgt gat gac tgt ttc aac gta ttt agg gaa ccc aac gta gct att      242
Val Cys Asp Asp Cys Phe Asn Val Phe Arg Glu Pro Asn Val Ala Ile
             65                  70                  75 gat tgc agg gag aac tgt tac aac aac gaa gtg ttc cgc cag tgc atg      290
Asp Cys Arg Glu Asn Cys Tyr Asn Asn Glu Val Phe Arg Gln Cys Met
         80                  85                  90 gca tac gtc gtt ccc gca aac ctc cac gac gaa cac agg caa gcc gtg      338
Ala Tyr Val Val Pro Ala Asn Leu His Asp Glu His Arg Gln Ala Val
     95                 100                 105 cag atg gtc ggc aag taa actacttc                                     364
Gln Met Val Gly Lys
110
```

<210> SEQ ID NO 2
<211> LENGTH: 114
<212> TYPE: PRT
<213> ORGANISM: Litopenaeus vannamei

<400> SEQUENCE: 2

```
Met Leu Ala Tyr Arg Thr Met Trp Ser Ala Ile Met Ala Ser Leu Leu
 1               5                  10                  15

Leu Leu Leu Ala Ala Ser Ser Ala Ala Pro Ala Asp Ala Leu Ser Ala
             20                  25                  30

Pro Ala Ala Gly Leu Thr Lys Arg Ser Leu Phe Asp Pro Ser Cys Ser
         35                  40                  45

Gly Val Phe Asp Arg Gln Leu Leu Arg Arg Leu Arg Arg Val Cys Asp
     50                  55                  60

Asp Cys Phe Asn Val Phe Arg Glu Pro Asn Val Ala Ile Asp Cys Arg
 65                  70                  75                  80

Glu Asn Cys Tyr Asn Asn Glu Val Phe Arg Gln Cys Met Ala Tyr Val
                 85                  90                  95

Val Pro Ala Asn Leu His Asp Glu His Arg Gln Ala Val Gln Met Val
            100                 105                 110

Gly Lys
```

<210> SEQ ID NO 3
<211> LENGTH: 450
<212> TYPE: DNA
<213> ORGANISM: Litopenaeus vannamei
<220> FEATURE:
<221> NAME/KEY: CDS
<222> LOCATION: (54)..(449)

<400> SEQUENCE: 3

```
gaagagcctc gaagtcgccg tctctcctcc cgattcgagt cgacgccgag gaa atg        56
                                                         Met
                                                           1 att ggg gtt cga ctg gtg cgt tca gct gtc ctg gta tcc ctg ctg cta      104
Ile Gly Val Arg Leu Val Arg Ser Ala Val Leu Val Ser Leu Leu Leu
        5                   10                  15 gtg ttc ccg gcc tct gtc ctc gcc tct tgg gac gga aat gaa atc cct      152
Val Phe Pro Ala Ser Val Leu Ala Ser Trp Asp Gly Asn Glu Ile Pro
            20                  25                  30 ccg tcc ctg cct tcc tcc tca gaa tcc tct cct gcg acc ccc ctc gcg      200
Pro Ser Leu Pro Ser Ser Ser Glu Ser Ser Pro Ala Thr Pro Leu Ala
 35                  40                  45 gga gcc cag acc gca aac aag cgc agc ata tcc ttc gac tcg tgc acg      248
Gly Ala Gln Thr Ala Asn Lys Arg Ser Ile Ser Phe Asp Ser Cys Thr
 50                  55                  60                  65 ggc gtc tac gac cgc gaa ctc ctt gta agg ctc gac cgc gtg tgc gaa      296
Gly Val Tyr Asp Arg Glu Leu Leu Val Arg Leu Asp Arg Val Cys Glu
                 70                  75                  80 gac tgc tac aac ctg tac cgc gac acc gac gtg gcg gtc gaa tgc agg      344
Asp Cys Tyr Asn Leu Tyr Arg Asp Thr Asp Val Ala Val Glu Cys Arg
             85                  90                  95 agc aac tgt ttc cac aac gag gta ttc ctg tac tgc gtc gac tac atg      392
Ser Asn Cys Phe His Asn Glu Val Phe Leu Tyr Cys Val Asp Tyr Met
        100                 105                 110 tac cgg cct cgc caa agg aac cag tac cgg gcc gcc ctg cag agg ctc      440
Tyr Arg Pro Arg Gln Arg Asn Gln Tyr Arg Ala Ala Leu Gln Arg Leu
    115                 120                 125 ggc aag tag g                                                        450
Gly Lys
130
```

<210> SEQ ID NO 4
<211> LENGTH: 131
<212> TYPE: PRT
<213> ORGANISM: Litopenaeus vannamei

<400> SEQUENCE: 4

```
Met Ile Gly Val Arg Leu Val Arg Ser Ala Val Leu Val Ser Leu Leu
  1               5                  10                  15

Leu Val Phe Pro Ala Ser Val Leu Ala Ser Trp Asp Gly Asn Glu Ile
             20                  25                  30

Pro Pro Ser Leu Pro Ser Ser Ser Glu Ser Ser Pro Ala Thr Pro Leu
         35                  40                  45

Ala Gly Ala Gln Thr Ala Asn Lys Arg Ser Ile Ser Phe Asp Ser Cys
     50                  55                  60

Thr Gly Val Tyr Asp Arg Glu Leu Leu Val Arg Leu Asp Arg Val Cys
 65                  70                  75                  80

Glu Asp Cys Tyr Asn Leu Tyr Arg Asp Thr Asp Val Ala Val Glu Cys
                 85                  90                  95

Arg Ser Asn Cys Phe His Asn Glu Val Phe Leu Tyr Cys Val Asp Tyr
            100                 105                 110

Met Tyr Arg Pro Arg Gln Arg Asn Gln Tyr Arg Ala Ala Leu Gln Arg
        115                 120                 125

Leu Gly Lys
        130
```

<210> SEQ ID NO 5

<211> LENGTH: 833
<212> TYPE: DNA
<213> ORGANISM: Litopenaeus vannamei
<220> FEATURE:
<221> NAME/KEY: CDS
<222> LOCATION: (45)..(389)

<400> SEQUENCE: 5

```
agtgccttca ccacatctaa aagccgttgt gatttacacg agct atg act gcc ttc         56
                                              Met Thr Ala Phe
                                                1 cgt atg gta tgg tca atg ttg ttg gct tct tta ctg ctg ctc gcg            104
Arg Met Val Trp Ser Met Leu Leu Ala Ser Leu Leu Leu Leu Ala
 5              10                 15                  20 gcg tcg tcc gct gcc ccc gcc gac gcc tta tcc gcc cct gcg gca ggc        152
Ala Ser Ser Ala Ala Pro Ala Asp Ala Leu Ser Ala Pro Ala Ala Gly
             25                  30                  35 ctc acc aaa cgc tcg ctc ttc gac cct tcc tgc acc ggc gtc ttc gac        200
Leu Thr Lys Arg Ser Leu Phe Asp Pro Ser Cys Thr Gly Val Phe Asp
         40                  45                  50 cgg cag ctc ttg cgg agg ctg cgt cga gtg tgt gac gac tgt ttc aac        248
Arg Gln Leu Leu Arg Arg Leu Arg Arg Val Cys Asp Asp Cys Phe Asn
             55                  60                  65 gta ttc agg gaa ccc aac gta tct act gaa tgc aga agt aac tgt tac        296
Val Phe Arg Glu Pro Asn Val Ser Thr Glu Cys Arg Ser Asn Cys Tyr
 70                  75                  80 aac aat gaa gtg ttc cgc cag tgt atg gaa tac ctc ctc ccg cct cac        344
Asn Asn Glu Val Phe Arg Gln Cys Met Glu Tyr Leu Leu Pro Pro His
 85                  90                  95                 100 ctt cac gaa gag cac aga cta gct gtc cag atg gtc ggg aaa tag            389
Leu His Glu Glu His Arg Leu Ala Val Gln Met Val Gly Lys
             105                 110 atttacggtt aagacgctgc aacccacttc gctgacgaca ggaattcgat gatagtaaaa       449
ggcaccctaa ttccacttat tctacagcat agcactgagt cctcgatcgc tgtaacgaat      509
ggttttcaat gctgaagact tatactatga aatgaagctg acttccactc taagaaataa      569
gaatgaaagg gtgcagtttg ccattatatt gggactatca tgacacattt agttcggcca      629
ctgatcacag tatagaaaat atatatacac atgaacgcca tttatcagga aactggagaa      689
aaaatatcac tgaaagagat tgttcttagg actcgaggct ttaattaaca ttagaatagg      749
tatttgtgat gttttattat gtttaaattt acgaataaag cactggcatg ctaaaaaaaa      809
aaaaaaaaaa aaaaaaaaaa aaaa                                             833
```

<210> SEQ ID NO 6
<211> LENGTH: 114
<212> TYPE: PRT
<213> ORGANISM: Litopenaeus vannamei

<400> SEQUENCE: 6

```
Met Thr Ala Phe Arg Met Val Trp Ser Met Leu Leu Ala Ser Leu Leu
 1               5                  10                  15

Leu Leu Leu Ala Ala Ser Ser Ala Ala Pro Ala Asp Ala Leu Ser Ala
             20                  25                  30

Pro Ala Ala Gly Leu Thr Lys Arg Ser Leu Phe Asp Pro Ser Cys Thr
         35                  40                  45

Gly Val Phe Asp Arg Gln Leu Leu Arg Arg Leu Arg Arg Val Cys Asp
     50                  55                  60

Asp Cys Phe Asn Val Phe Arg Glu Pro Asn Val Ser Thr Glu Cys Arg
 65                  70                  75                  80
```

```
Ser Asn Cys Tyr Asn Asn Glu Val Phe Arg Gln Cys Met Glu Tyr Leu
                85                  90                  95

Leu Pro Pro His Leu His Glu His Arg Leu Ala Val Gln Met Val
            100                 105                 110

Gly Lys
```

<210> SEQ ID NO 7
<211> LENGTH: 404
<212> TYPE: DNA
<213> ORGANISM: Litopenaeus vannamei
<220> FEATURE:
<221> NAME/KEY: CDS
<222> LOCATION: (49)..(402)

<400> SEQUENCE: 7

```
gaaaggacct cgttgcaatt gagtatttcg agtttcgcgt catttaca atg gta ctt        57
                                                  Met Val Leu
                                                   1 caa tac atg ctg tct gcg gcc ctg ctg gtg ctc gcc gcc tcg tcc tcg       105
Gln Tyr Met Leu Ser Ala Ala Leu Leu Val Leu Ala Ala Ser Ser Ser
 5                  10                  15 ccc gcc gcc gcc cgc tcc ctc gac gcg gcg cct tcg tct gcg tcc tca       153
Pro Ala Ala Ala Arg Ser Leu Asp Ala Ala Pro Ser Ser Ala Ser Ser
20                  25                  30                  35 gga agc cac agc ctc agc aag cgc tcc ctc ttc gac ccg gcg tgc acc       201
Gly Ser His Ser Leu Ser Lys Arg Ser Leu Phe Asp Pro Ala Cys Thr
                40                  45                  50 ggc atc tac gac cgg cag ctg ctg ggc aag ctg ggg cgc ctg tgc gac       249
Gly Ile Tyr Asp Arg Gln Leu Leu Gly Lys Leu Gly Arg Leu Cys Asp
            55                  60                  65 gac tgc tac aac gtg ttc cgg gag ccc aag gtg gcc acg gga tgc agg       297
Asp Cys Tyr Asn Val Phe Arg Glu Pro Lys Val Ala Thr Gly Cys Arg
        70                  75                  80 agt aac tgc tac tac aac ctc atc ttc ctc gac tgc ctc gag tac ctg       345
Ser Asn Cys Tyr Tyr Asn Leu Ile Phe Leu Asp Cys Leu Glu Tyr Leu
    85                  90                  95 atc ccg agc cac ctt cag gag gag cac atg tcg gcc ctg cag acc gtc       393
Ile Pro Ser His Leu Gln Glu Glu His Met Ser Ala Leu Gln Thr Val
100                 105                 110                 115 ggc aaa taa ag                                                        404
Gly Lys
```

<210> SEQ ID NO 8
<211> LENGTH: 117
<212> TYPE: PRT
<213> ORGANISM: Litopenaeus vannamei

<400> SEQUENCE: 8

```
Met Val Leu Gln Tyr Met Leu Ser Ala Ala Leu Leu Val Leu Ala Ala
 1               5                  10                  15

Ser Ser Ser Pro Ala Ala Ala Arg Ser Leu Asp Ala Ala Pro Ser Ser
            20                  25                  30

Ala Ser Ser Gly Ser His Ser Leu Ser Lys Arg Ser Leu Phe Asp Pro
        35                  40                  45

Ala Cys Thr Gly Ile Tyr Asp Arg Gln Leu Leu Gly Lys Leu Gly Arg
    50                  55                  60

Leu Cys Asp Asp Cys Tyr Asn Val Phe Arg Glu Pro Lys Val Ala Thr
65                  70                  75                  80

Gly Cys Arg Ser Asn Cys Tyr Tyr Asn Leu Ile Phe Leu Asp Cys Leu
```

```
                    85                  90                  95
Glu Tyr Leu Ile Pro Ser His Leu Gln Glu His Met Ser Ala Leu
            100                 105                 110

Gln Thr Val Gly Lys
        115

<210> SEQ ID NO 9
<211> LENGTH: 587
<212> TYPE: DNA
<213> ORGANISM: Litopenaeus vannamei
<220> FEATURE:
<221> NAME/KEY: CDS
<222> LOCATION: (60)..(416)

<400> SEQUENCE: 9
ggtcgcagtc acagtcgcca gctgctcata ctctgaactc ttgacacaga ctgctcgcc       59 atg aca gcc ttt cgc ttg atg gcc gtg gcc ctg gtg gtg gtc gtg gcg      107
Met Thr Ala Phe Arg Leu Met Ala Val Ala Leu Val Val Val Val Ala
1               5                   10                  15 tgc tcg acg acc tgg gct cgc tcc gcc gag ggg tcg tcg tcc ccc gtg      155
Cys Ser Thr Thr Trp Ala Arg Ser Ala Glu Gly Ser Ser Ser Pro Val
                20                  25                  30 gcc tcc ctc atc agg ggc cgc agc ctc agc aag cga gca aac ttc gac      203
Ala Ser Leu Ile Arg Gly Arg Ser Leu Ser Lys Arg Ala Asn Phe Asp
            35                  40                  45 cct tcc tgc acg ggc gtc tac gac cgg gag ctc ctg ggg agg ctg agc      251
Pro Ser Cys Thr Gly Val Tyr Asp Arg Glu Leu Leu Gly Arg Leu Ser
        50                  55                  60 cgc ctc tgc gac gac tgc tac aac gtg ttt cgc gag ccc aag gtg gcc      299
Arg Leu Cys Asp Asp Cys Tyr Asn Val Phe Arg Glu Pro Lys Val Ala
65                  70                  75                  80 acg gag tgc agg agc aac tgc ttc tac aac ccc gtg ttc gtc cag tgc      347
Thr Glu Cys Arg Ser Asn Cys Phe Tyr Asn Pro Val Phe Val Gln Cys
                85                  90                  95 ctg gag tac ctg att ccg gcc gac ctg cac gag gag tac caa gcc ctc      395
Leu Glu Tyr Leu Ile Pro Ala Asp Leu His Glu Glu Tyr Gln Ala Leu
            100                 105                 110 gtg cag acg gtg ggc aag tag gctcgctcga cctgccacgg cctcgcctcg          446
Val Gln Thr Val Gly Lys
        115 cgcactcacg ccaacggccg gaagacacag agaggatttc aggatttgtt tctggctaac    506 tggtgtattt catcgaccct gctcggattt tgatatgatt tctcatgtcc taaattgtga    566 tgaatctcta aatgaagtgt g                                              587

<210> SEQ ID NO 10
<211> LENGTH: 118
<212> TYPE: PRT
<213> ORGANISM: Litopenaeus vannamei

<400> SEQUENCE: 10

Met Thr Ala Phe Arg Leu Met Ala Val Ala Leu Val Val Val Val Ala
1               5                   10                  15

Cys Ser Thr Thr Trp Ala Arg Ser Ala Glu Gly Ser Ser Ser Pro Val
                20                  25                  30

Ala Ser Leu Ile Arg Gly Arg Ser Leu Ser Lys Arg Ala Asn Phe Asp
            35                  40                  45

Pro Ser Cys Thr Gly Val Tyr Asp Arg Glu Leu Leu Gly Arg Leu Ser
        50                  55                  60
```

```
Arg Leu Cys Asp Asp Cys Tyr Asn Val Phe Arg Glu Pro Lys Val Ala
 65                  70                  75                  80

Thr Glu Cys Arg Ser Asn Cys Phe Tyr Asn Pro Val Phe Val Gln Cys
                 85                  90                  95

Leu Glu Tyr Leu Ile Pro Ala Asp Leu His Glu Glu Tyr Gln Ala Leu
            100                 105                 110

Val Gln Thr Val Gly Lys
        115

<210> SEQ ID NO 11
<211> LENGTH: 43
<212> TYPE: DNA
<213> ORGANISM: Artificial
<220> FEATURE:
<223> OTHER INFORMATION: Primer

<400> SEQUENCE: 11
taatacgact cactataggg agagcatcga cttcaaggag gac            43

<210> SEQ ID NO 12
<211> LENGTH: 43
<212> TYPE: DNA
<213> ORGANISM: Artificial
<220> FEATURE:
<223> OTHER INFORMATION: Primer

<400> SEQUENCE: 12
taatacgact cactataggg agatgggtgc tcaggtagtg gtt            43

<210> SEQ ID NO 13
<211> LENGTH: 41
<212> TYPE: DNA
<213> ORGANISM: Artificial
<220> FEATURE:
<223> OTHER INFORMATION: Primer

<400> SEQUENCE: 13
taatacgact cactataggg agaaagcgag caaacttcga c              41

<210> SEQ ID NO 14
<211> LENGTH: 41
<212> TYPE: DNA
<213> ORGANISM: Artificial
<220> FEATURE:
<223> OTHER INFORMATION: Primer

<400> SEQUENCE: 14
taatacgact cactataggg agactacttg cccaccgtct g              41

<210> SEQ ID NO 15
<211> LENGTH: 42
<212> TYPE: DNA
<213> ORGANISM: Artificial
<220> FEATURE:
<223> OTHER INFORMATION: Primer

<400> SEQUENCE: 15
taatacgact cactataggg agactcgctc ttcgaccctt cc             42

<210> SEQ ID NO 16
<211> LENGTH: 42
<212> TYPE: DNA
<213> ORGANISM: Artificial
<220> FEATURE:
<223> OTHER INFORMATION: Primer
```

-continued

```
<400> SEQUENCE: 16
taatacgact cactataggg agactatttc ccgaccatct gg                            42

<210> SEQ ID NO 17
<211> LENGTH: 45
<212> TYPE: DNA
<213> ORGANISM: Artificial
<220> FEATURE:
<223> OTHER INFORMATION: Primer

<400> SEQUENCE: 17
taatacgact cactataggg agacgcagca tatccttcga ctcgt                         45

<210> SEQ ID NO 18
<211> LENGTH: 42
<212> TYPE: DNA
<213> ORGANISM: Artificial
<220> FEATURE:
<223> OTHER INFORMATION: Primer

<400> SEQUENCE: 18
taatacgact cactataggg agaaagcgct ccctcttcga cc                            42

<210> SEQ ID NO 19
<211> LENGTH: 47
<212> TYPE: DNA
<213> ORGANISM: Artificial
<220> FEATURE:
<223> OTHER INFORMATION: Primer

<400> SEQUENCE: 19
taatacgact cactataggg agactttatt tgccgacggt ctgcagg                       47

<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20
taatacgact cactataggg                                                     20

<210> SEQ ID NO 21
<211> LENGTH: 19
<212> TYPE: DNA
<213> ORGANISM: Artificial
<220> FEATURE:
<223> OTHER INFORMATION: Primer

<400> SEQUENCE: 21
cggagtgcag gagcaactg                                                      19

<210> SEQ ID NO 22
<211> LENGTH: 25
<212> TYPE: DNA
<213> ORGANISM: Artificial
<220> FEATURE:
<223> OTHER INFORMATION: Primer

<400> SEQUENCE: 22
cctctctgtg tcttctggcc gttgg                                               25

<210> SEQ ID NO 23
```

<211> LENGTH: 27
<212> TYPE: DNA
<213> ORGANISM: Artificial
<220> FEATURE:
<223> OTHER INFORMATION: Primer

<400> SEQUENCE: 23
cgacctcaca gactacctga tgaagat                                27

<210> SEQ ID NO 24
<211> LENGTH: 21
<212> TYPE: DNA
<213> ORGANISM: Artificial
<220> FEATURE:
<223> OTHER INFORMATION: Primer

<400> SEQUENCE: 24
gtggtcatct cctgctcgaa g                                     21

<210> SEQ ID NO 25
<211> LENGTH: 26
<212> TYPE: DNA
<213> ORGANISM: Artificial
<220> FEATURE:
<223> OTHER INFORMATION: Primer

<400> SEQUENCE: 25
tctacaaccc cgtgttcgtc cagtgc                                26

<210> SEQ ID NO 26
<211> LENGTH: 29
<212> TYPE: DNA
<213> ORGANISM: Artificial
<220> FEATURE:
<223> OTHER INFORMATION: Primer

<400> SEQUENCE: 26
cgaccaccgc cgagcgagaa atcgttcgt                             29

<210> SEQ ID NO 27
<211> LENGTH: 19
<212> TYPE: DNA
<213> ORGANISM: Artificial
<220> FEATURE:
<223> OTHER INFORMATION: Primer

<400> SEQUENCE: 27
ctcgctattc gacccttcc                                        19

<210> SEQ ID NO 28
<211> LENGTH: 234
<212> TYPE: DNA
<213> ORGANISM: Litopenaeus vannamei

<400> SEQUENCE: 28
ctcgctattc gacccttcct gcagcggcgt cttcgaccgg cagctcttgc ggaggctgcg    60
tcgagtgtgt gatgactgtt tcaacgtatt tagggaaccc aacgtagcta ttgattgcag   120
ggagaactgt tacaacaacg aagtgttccg ccagtgcatg gcatacgtcg ttcccgcaaa   180
cctccacgac gaacacaggc aagccgtgca gatggtcggc aagtaaacta cttc         234

<210> SEQ ID NO 29
<211> LENGTH: 22
<212> TYPE: DNA
<213> ORGANISM: Artificial

```
<220> FEATURE:
<223> OTHER INFORMATION: Primer

<400> SEQUENCE: 29
cgcagcatat ccttcgactc gt                                             22

<210> SEQ ID NO 30
<211> LENGTH: 229
<212> TYPE: DNA
<213> ORGANISM: Litopenaeus vannamei

<400> SEQUENCE: 30
cgcagcatat ccttcgactc gtgcacgggc gtctacgacc gcgaactcct tgtaaggctc    60
gaccgcgtgt gcgaagactg ctacaacctg taccgcgaca ccgacgtggc ggtcgaatgc   120
aggagcaact gtttccacaa cgaggtattc ctgtactgcg tcgactacat gtaccggcct   180
cgccaaagga accagtaccg ggccgccctg cagaggctcg gcaagtagg               229

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
ctcgctcttc gacccttcct                                                20

<210> SEQ ID NO 32
<211> LENGTH: 19
<212> TYPE: DNA
<213> ORGANISM: Artificial
<220> FEATURE:
<223> OTHER INFORMATION: Primer

<400> SEQUENCE: 32
ccagatggtc gggaaatag                                                 19

<210> SEQ ID NO 33
<211> LENGTH: 226
<212> TYPE: DNA
<213> ORGANISM: Litopenaeus vannamei

<400> SEQUENCE: 33
ctcgctcttc gacccttcct gcaccggcgt cttcgaccgg cagctcttgc ggaggctgcg    60
tcgagtgtgt gacgactgtt tcaacgtatt cagggaaccc aacgtatcta ctgaatgcag   120
aagtaactgt tacaacaatg aagtgttccg ccagtgtatg gaatacctcc tcccgcctca   180
ccttcacgaa gagcacagac tagctgtcca gatggtcggg aaatag                  226

<210> SEQ ID NO 34
<211> LENGTH: 19
<212> TYPE: DNA
<213> ORGANISM: Artificial
<220> FEATURE:
<223> OTHER INFORMATION: Primer

<400> SEQUENCE: 34
aagcgctccc tcttcgacc                                                 19

<210> SEQ ID NO 35
<211> LENGTH: 24
<212> TYPE: DNA
```

```
<213> ORGANISM: Artificial
<220> FEATURE:
<223> OTHER INFORMATION: Primer

<400> SEQUENCE: 35
cctgcagacc gtcggcaaat aaag                                          24

<210> SEQ ID NO 36
<211> LENGTH: 233
<212> TYPE: DNA
<213> ORGANISM: Litopenaeus vannamei

<400> SEQUENCE: 36
aagcgctccc tcttcgaccc ggcgtgcacc ggcatctacg accggcagct gctgggcaag   60
ctggggcgcc tgtgcgacga ctgctacaac gtgttccggg agcccaaggt ggccacggga  120
tgcaggagta actgctacta caacctcatc ttcctcgact gcctcgagta cctgatcccg  180
agccaccttc aggaggagca catgtcggcc ctgcagaccg tcggcaaata aag         233

<210> SEQ ID NO 37
<211> LENGTH: 18
<212> TYPE: DNA
<213> ORGANISM: Artificial
<220> FEATURE:
<223> OTHER INFORMATION: Primer

<400> SEQUENCE: 37
aagcgagcaa acttcgac                                                 18

<210> SEQ ID NO 38
<211> LENGTH: 18
<212> TYPE: DNA
<213> ORGANISM: Artificial
<220> FEATURE:
<223> OTHER INFORMATION: Primer

<400> SEQUENCE: 38
cagacggtgg gcaagtag                                                 18

<210> SEQ ID NO 39
<211> LENGTH: 231
<212> TYPE: DNA
<213> ORGANISM: Litopenaeus vannamei

<400> SEQUENCE: 39
aagcgagcaa acttcgaccc ttcctgcacg ggcgtctacg accgggagct cctggggagg   60
ctgagccgcc tctgcgacga ctgctacaac gtgtttcgcg agcccaaggt ggccacggag  120
tgcaggagca actgcttcta caccccgtg ttcgtccagt gcctggagta cctgattccg   180
gccgacctgc acgaggagta ccaagccctc gtgcagacgg tgggcaagta g           231
```